United States Patent
Anderson

(10) Patent No.: US 9,782,251 B2
(45) Date of Patent: *Oct. 10, 2017

(54) INVERSE BELLOW INSERTION DEVICE

(71) Applicant: Robert G. Anderson, Aledo, TX (US)

(72) Inventor: Robert G. Anderson, Aledo, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/154,003

(22) Filed: May 13, 2016

(65) Prior Publication Data

US 2016/0250019 A1    Sep. 1, 2016

Related U.S. Application Data

(62) Division of application No. 14/969,364, filed on Dec. 15, 2015, now Pat. No. 9,474,593.

(51) Int. Cl.
*A61F 2/12* (2006.01)

(52) U.S. Cl.
CPC ...................................... *A61F 2/12* (2013.01)

(58) Field of Classification Search
CPC ......... A61F 2/12; A61L 27/18; A61L 2430/04
See application file for complete search history.

(56) References Cited

U.S. PATENT DOCUMENTS

| | | | |
|---|---|---|---|
| 4,641,648 A | 2/1987 | Shapiro | |
| 4,955,906 A | 9/1990 | Coggins et al. | |
| 5,571,178 A | 11/1996 | Ledergerber | |
| 5,723,006 A | 3/1998 | Ledergerber | |
| 5,782,913 A | 7/1998 | Schindler et al. | |
| 8,206,443 B2 | 6/2012 | Preissman | |
| 8,211,173 B2 | 7/2012 | Keller et al. | |
| 8,313,760 B2 | 11/2012 | Hunter | |
| 8,550,090 B2 | 10/2013 | Keller et al. | |
| 8,555,893 B2 | 10/2013 | Keller et al. | |
| 8,641,758 B1 | 2/2014 | Anderson | |
| D738,490 S | 9/2015 | Anderson | |
| 2007/0276484 A1 | 11/2007 | Abell et al. | |
| 2009/0204107 A1 | 8/2009 | Keller et al. | |
| 2010/0280610 A1 | 11/2010 | Preissman | |
| 2011/0035003 A1 | 2/2011 | Preissman | |
| 2011/0218624 A1 | 9/2011 | Preissman | |
| 2012/0185042 A1 | 7/2012 | Preissman | |
| 2012/0259414 A1 | 10/2012 | Preissman | |
| 2013/0073040 A1 | 3/2013 | Preissman | |

(Continued)

FOREIGN PATENT DOCUMENTS

WO    WO/2013/122568 A1    8/2013

OTHER PUBLICATIONS

Richard A. Mladick, M.D., F.A.C.S. "No-Touch" Submuscular Saline Breast Augmentation Technique, Aesthetic Plastic Surgery, 17:183-192, 1993 , New York, NY.

(Continued)

*Primary Examiner* — Thomas J Sweet
*Assistant Examiner* — Tiffany Shipmon
(74) *Attorney, Agent, or Firm* — Kirby B. Drake; Klemchuk LLP

(57) ABSTRACT

An apparatus and method for inserting prosthesis implants into a patient pocket. The apparatus has three openings including a prosthesis opening, a larger proximal opening, and a small distal opening. The apparatus prevents infection; eases insertion and placement; and reduces complications. In use, the inverse bellow is placed through the patient incision while allowing the bellow to be manipulated to force the prosthesis into a surgical pocket of a patient.

3 Claims, 10 Drawing Sheets

(56) References Cited

U.S. PATENT DOCUMENTS

Figure 1:
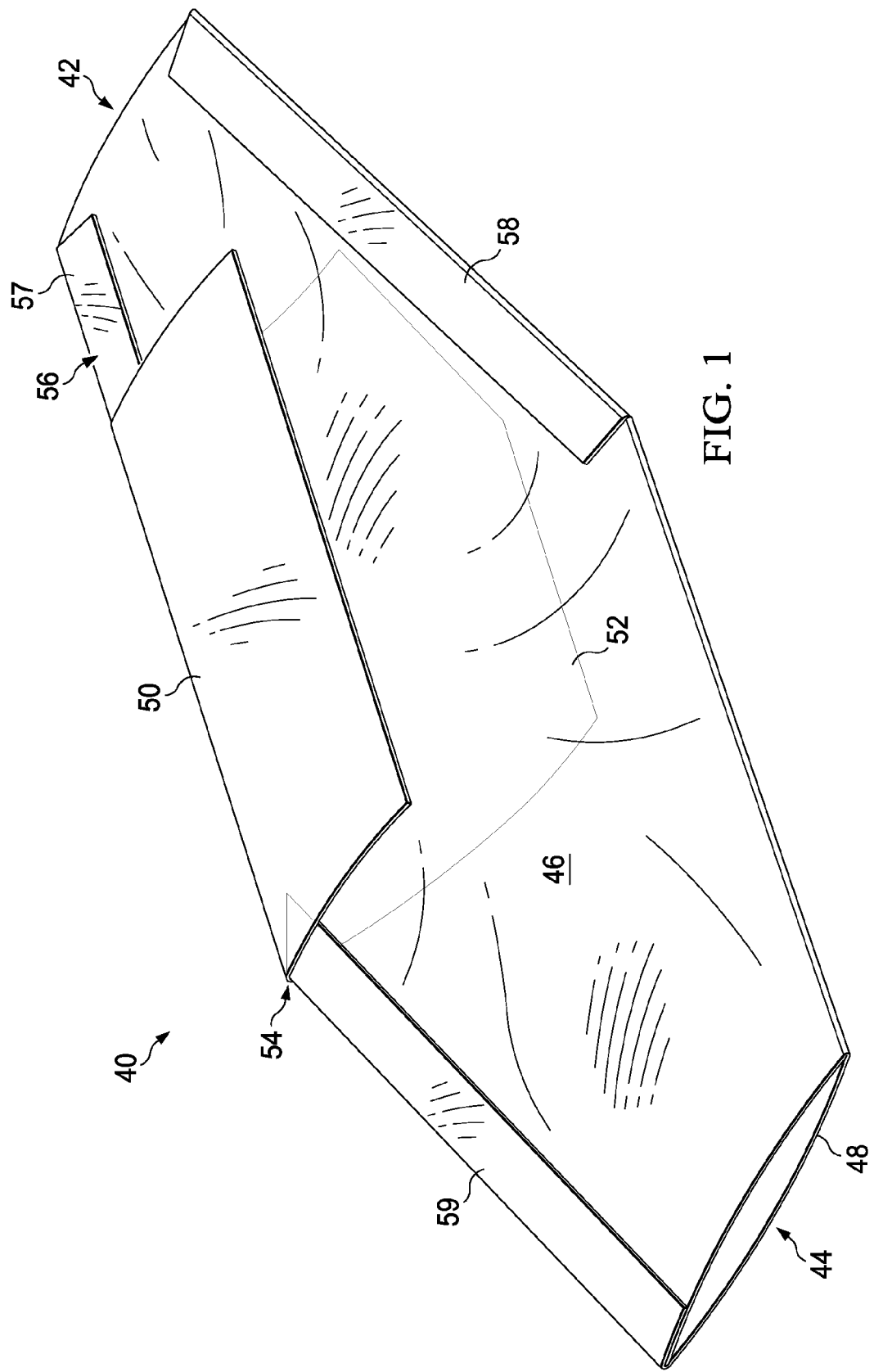

| 2014/0074235 A1 | 3/2014 | Keller et al. |
| 2014/0074236 A1 | 3/2014 | Keller et al. |
| 2014/0148901 A1 | 5/2014 | Anderson |
| 2016/0038275 A1 | 2/2016 | Preissman |

OTHER PUBLICATIONS

Richard A. Mladick, M.D., F.A.C.S. Significance of *Staphylococcus epidermidis* Causing Subclinical Infection, Plastic & Reconstructive Surgery: Apr. 15, 2005—vol. 115—Issue 5—pp. 1426-1427, Virginia Beach, VA.

"Richard A. Mladick, M.D., F.A.C.S. Prevention of Capsular Contracture, Plastic & Reconstructive Surgery: May 1999—vol. 103—Issue 6—pp. 1773-1774, Virginia Beach, VA".

Thomas M. Biggs, M.D. Prefilled Saline Breast Implants Offer Significant Advantages, Aesthetic Surgery Journal Sep. 1999 vol. 19 No. 5 424, St Louis, MO.

"Mitchel H. Brown, M.D.., M.Ed. Cohesive Silicone Gel Breast Implants in Aesthetic and Reconstructive Breast Surgery, Plastic & Reconstructive Surgery: Sep. 1, 2005—vol. 116—Issue 3—pp. 768-779".

"Mitchel H. Brown, M.D.., M.Ed. Cohesive Silicone Gel Breast Implants in Aesthetic and Reconstructive Breast Surgery,Plastic & Reconstructive Surgery: Sep. 1, 2005—vol. 116—Issue 3—pp. 768-779".

INVERSE BELLOW INSERTION DEVICE

CROSS-REFERENCE TO RELATED APPLICATIONS

This application is a divisional of U.S. patent application Ser. No. 14/969,364, filed Dec. 15, 2015, which claims priority provisional application Ser. No. 62/100,572 filed on Jan. 7, 2015, the disclosures of which is hereby incorporated by reference in its entirety.

BACKGROUND

Field of Invention

The invention relating to the apparatus and method of safely inserting a prosthesis into a human body.

Background of the Invention

The present invention is a useful and novel apparatus for simplifying prosthesis implant surgery, such as a breast implant, while preventing inadvertent dislodging of the implant from the distal openings.

Breast implants are a manufactured prosthesis used in cosmetic and reconstructive surgery. A breast implant is gelatinous, having an outer casing or membrane and an inner fluid substance such as saline or silicone.

Most implant procedures today do not use an insertion device. The surgeon makes the incision, creates a pocket for the implant, retracts the incision and then manually pushes the implant into the pocket. A saline implant can be inserted into a pocket in an empty configuration; once placed in the pocket, the implant is then filled with saline solution.

Preferably, the incision in the patient is as short as possible. Shorter incisions are less unsightly. This goal of a shorter incision is easier to accomplish with a saline implant. A saline implant is relatively easy to insert through a short incision, as the bladder is unfilled and therefore small in size as it passes through the incision. In contrast, silicone implants are prefilled resulting in a more difficult and complications-susceptible operation.

The incision is made in one of four places: in the armpit, in the breast fold, in the navel, or around the areola. Except for the navel insertion, one incision is made for each implant. Next, the surgeon dissects a path through the tissue to the desired destination of the implant. Once that path has been created, a pocket is created for the implant superficial or deep to the pectoralis major muscle.

The pocket may be formed in one of two places under the breast: subglandular (between the breast tissue and pectoralis major muscle) or subpectoral (under the pectoralis major muscle). Subglandular places the prosthesis directly behind the mammary gland and in front of the muscle. Subpectoral places the implant partially under the pectoralis major muscle. Due to the structure of the pectoralis major muscle, a portion of the implant is not covered by the muscle.

For inflatable implants, the surgeon rolls up the implant like a cigar and pushes it through the incision and into the pocket. The surgeon then uses a tube to fill the implant with saline.

For pre-filled implants, the procedure requires a larger incision length. The implant is then manually pushed through the incision into the pocket.

Secondary surgeries are common for patients with breast implants. And every additional surgery has risks due to anesthesia, infection or bleeding. In particular, patients with breast implants may require surgery to change the placement (from subglandular to subpectoral or vice versa), correct palpable folding of the implant, remove a ruptured implant; treat infection, bleeding, breast pain, contracted scar tissue forming around the implant and collections of fluid around the implant. The overall complication rate is about 20% for silicone gel breast augmentation with the majority of re-operations related to implant rupture (leakage), bleeding or capsular contracture.

Infection, or Cellulitis, occurs in 2%-4% of patients, with some surgeons reporting much higher rates, and is usually from the bacteria normally present on the skin. Symptoms of infection include fever, pain, swelling and redness. To reduce infection, surgeons give a single dose of antibiotics before the surgery, and use an antibiotic solution in the wound before implant placement. The antibiotic solution may double as lubrication to allow easier insertion of the implant into the pocket. However, surgeons can bring the rate of infection down further by preventing the implant from touching the patient's skin.

The implant insertion devices heretofore known suffer from a number of disadvantages:
1. Requires the surgeon to resize the insertion device to match different implant sizes.
2. Relies on the correct trimming (alteration) by the surgeon. The implant company and insertion device company have no control over the surgeon. If the surgeon does not alter the device properly, unsafe damaging pressure may be applied to the implant during the insertion process.
3. Distal end of the device is large enough for the implant to inadvertently slip out of the device.
4. Due to the high cost, encourages re-use despite the manufacturer recommendation not to do so.

SUMMARY OF THE INVENTION

An invention, which meets the needs stated above, is a system and method to insert a prosthesis into a patient. The method allows the surgeon greater control over the implant while reducing the chance of surgical and post-surgery complications.

Objects and Advantages

Accordingly, besides the objects and advantages of the system for a breast implant insertion device described above, several objects and advantages of the present invention are:
a) to provide a tool that does not have to be trimmed (altered) by the surgeon;
b) to provide a single tool that fits all sizes of implants;
c) to provide a easier manipulation of the insertion device;
d) to provide a simplified insertion method;
e) to provide a safe maximum pressure applied to the breast implant.

Further objects and advantages of this invention will become apparent from a consideration of the drawings and the ensuing description of the drawings.

DRAWING FIGURES

Figure 2:
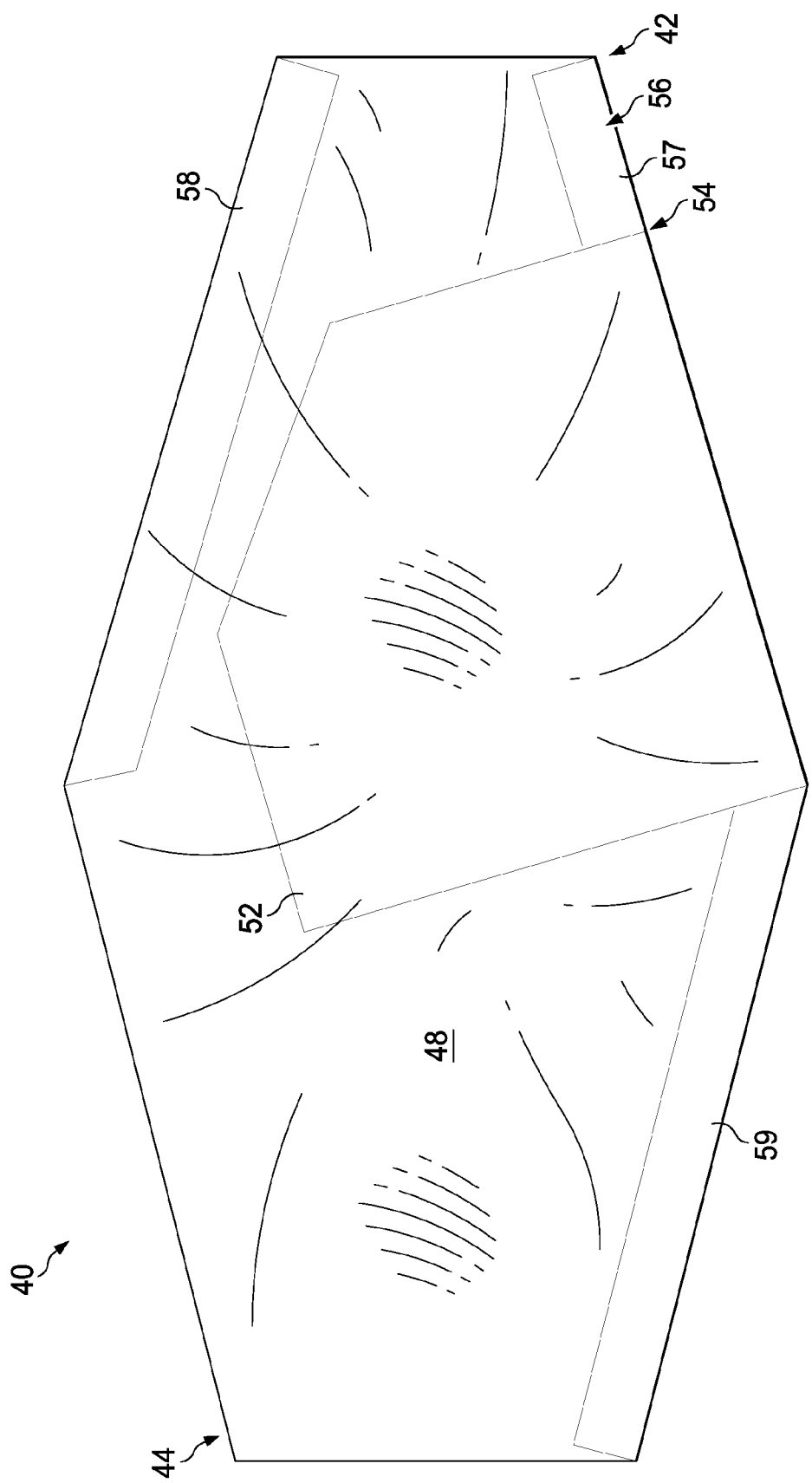

The accompanying drawings, which are incorporated in and constitute a part of this specification, illustrate embodiments of the present invention and together with the description, serve to explain the principles of this invention. In the figures:

FIG. 1: Top side perspective view of an inverse bellow.
FIG. 2: Bottom view of an inverse bellow.

Figure 3:
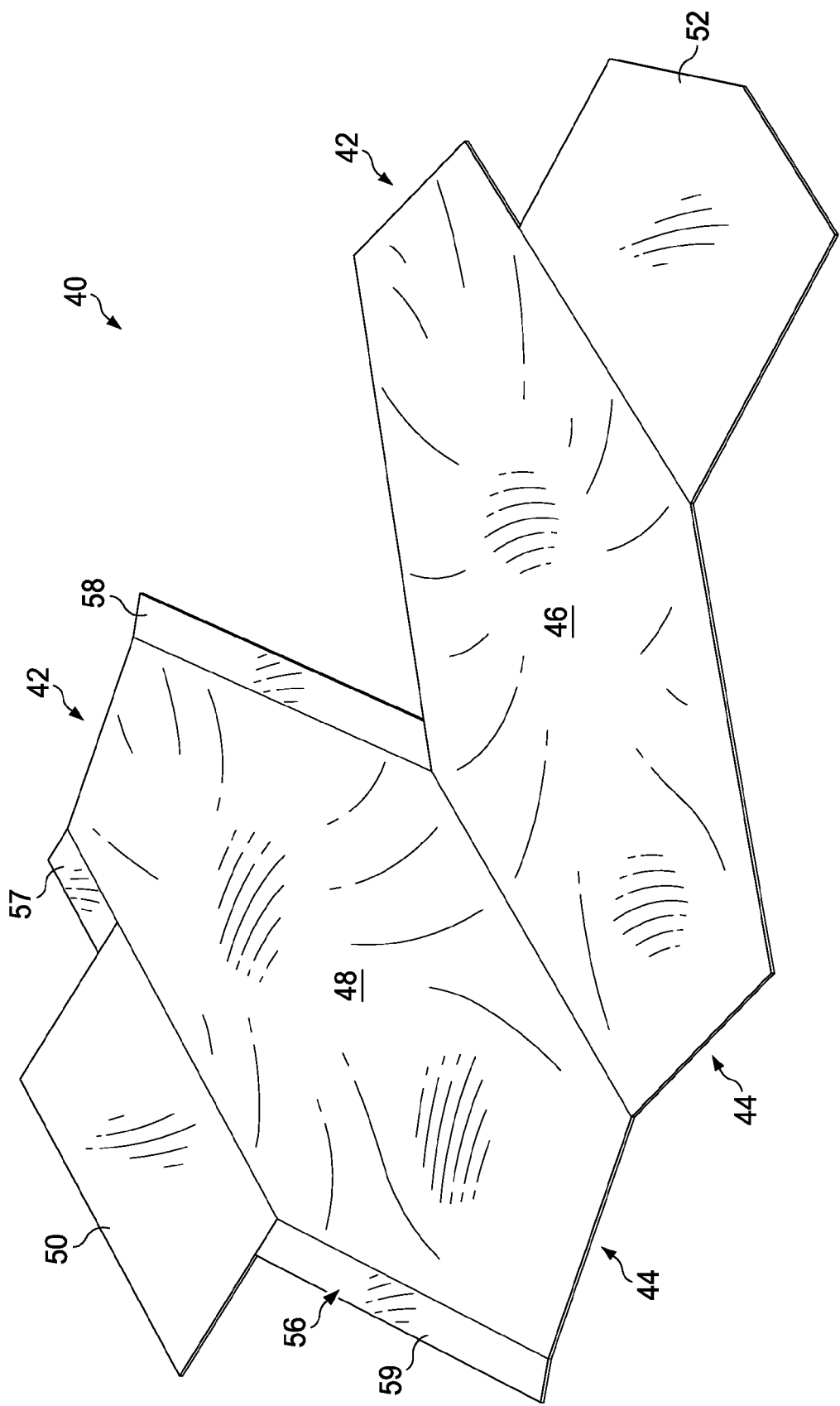

FIG. 3: Top side perspective view of an inverse bellow, unassembled.

Figure 4A:
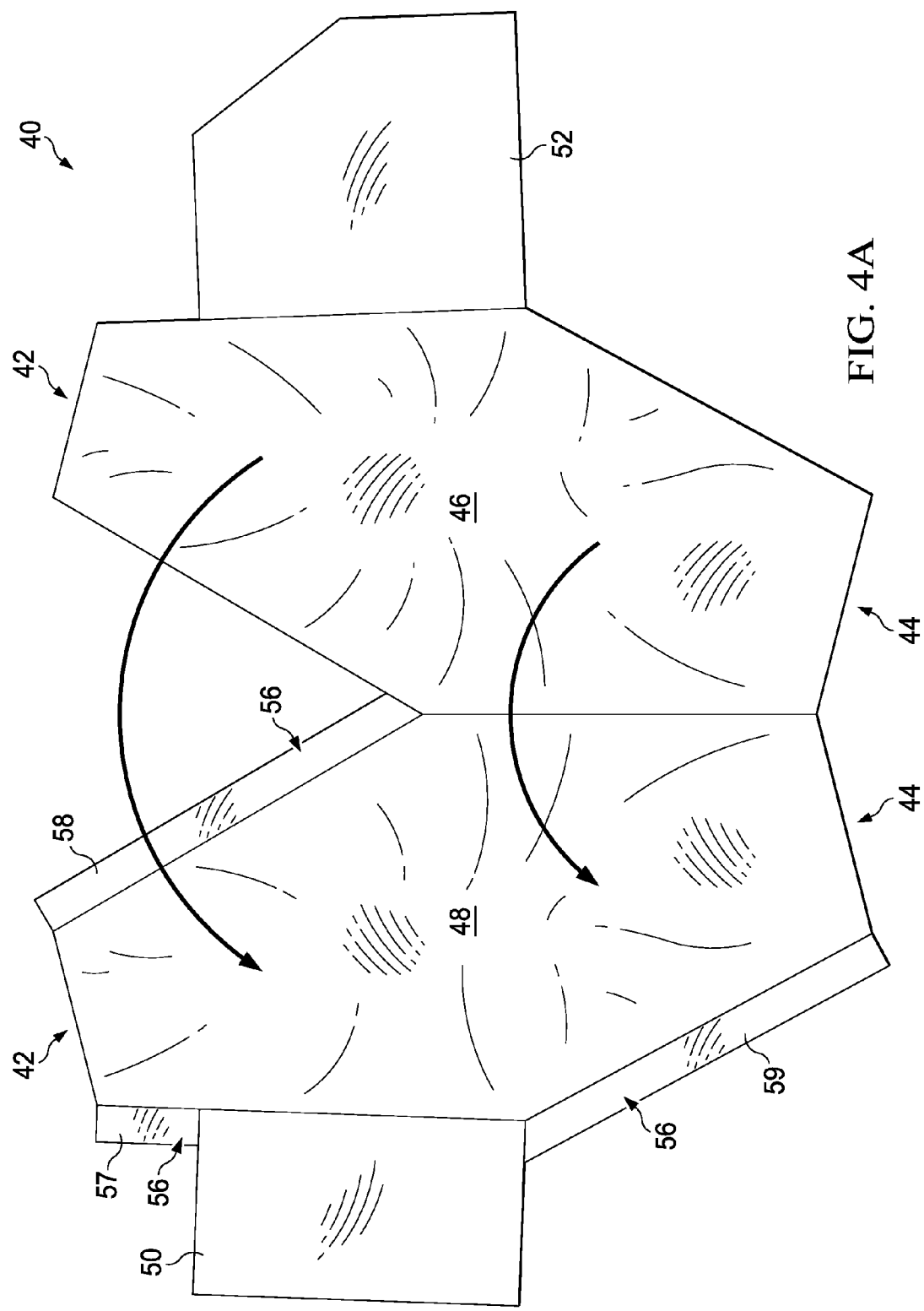

FIG. 4A: Top view of an inverse bellow, with a fold along the abutted edges.

Figure 4B:
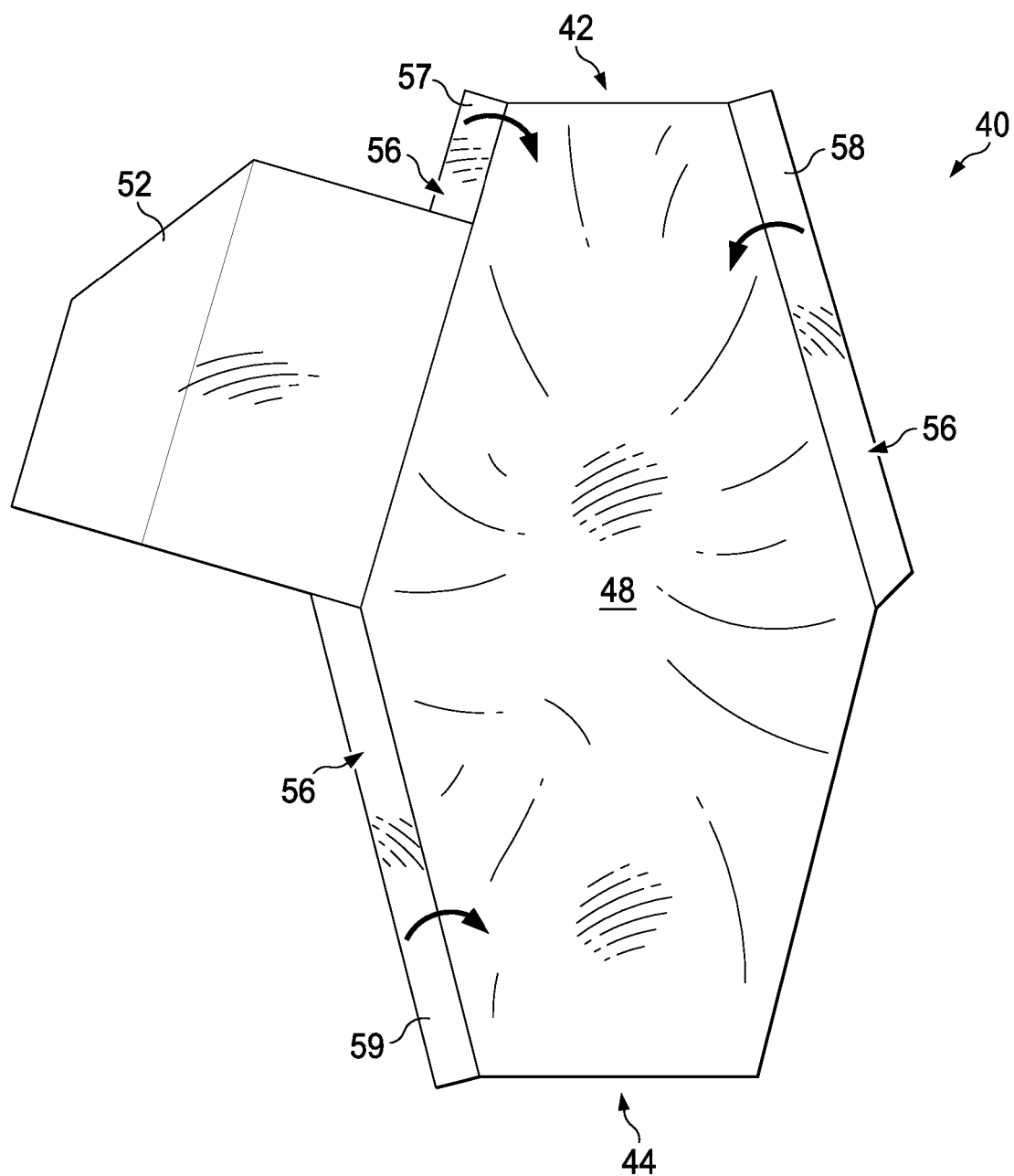

FIG. 4B: Top view of an inverse bellow showing the folding of the seal folds.

Figure 4C:
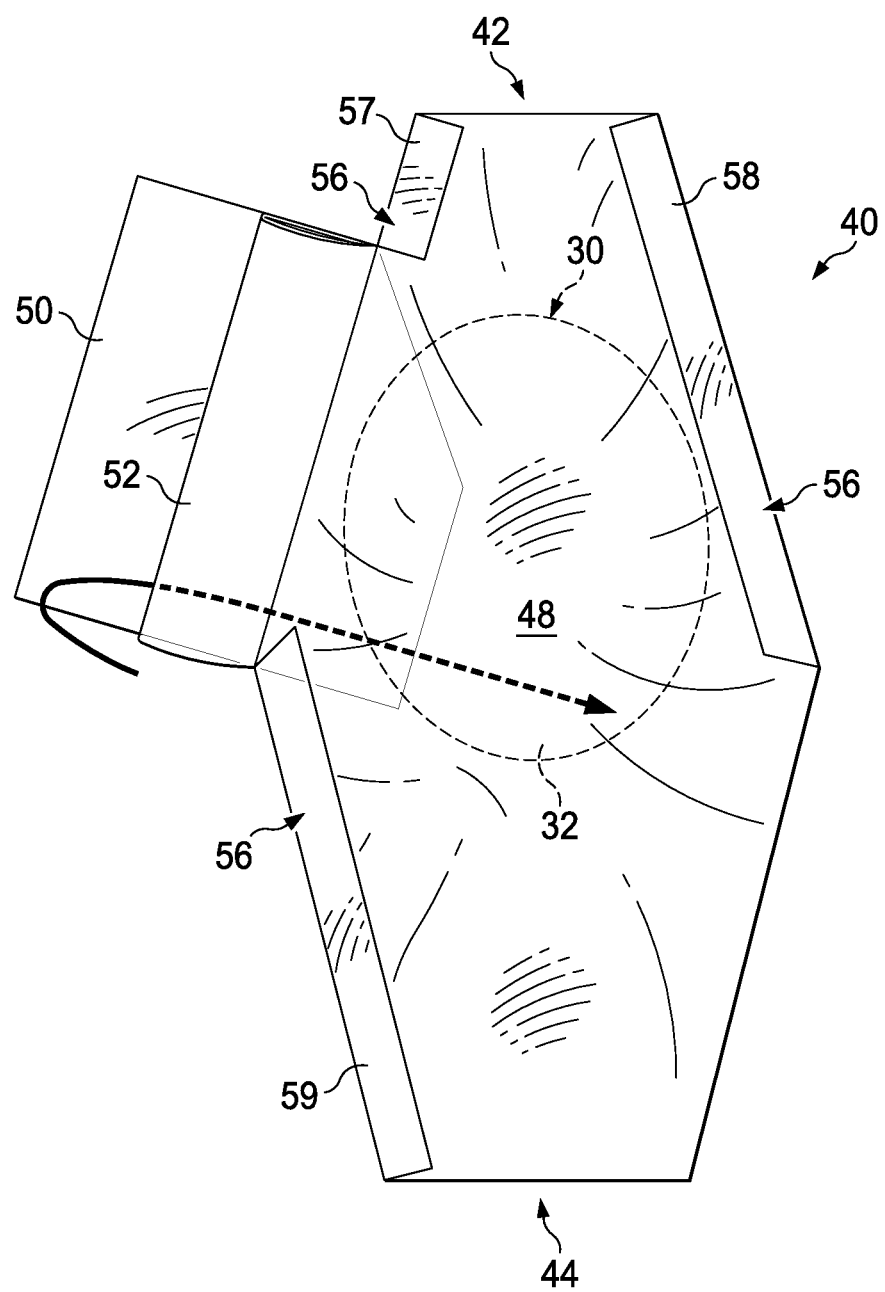

FIG. 4C: Top view of an inverse bellow, internal tab placed through prosthesis opening.

Figure 4D:
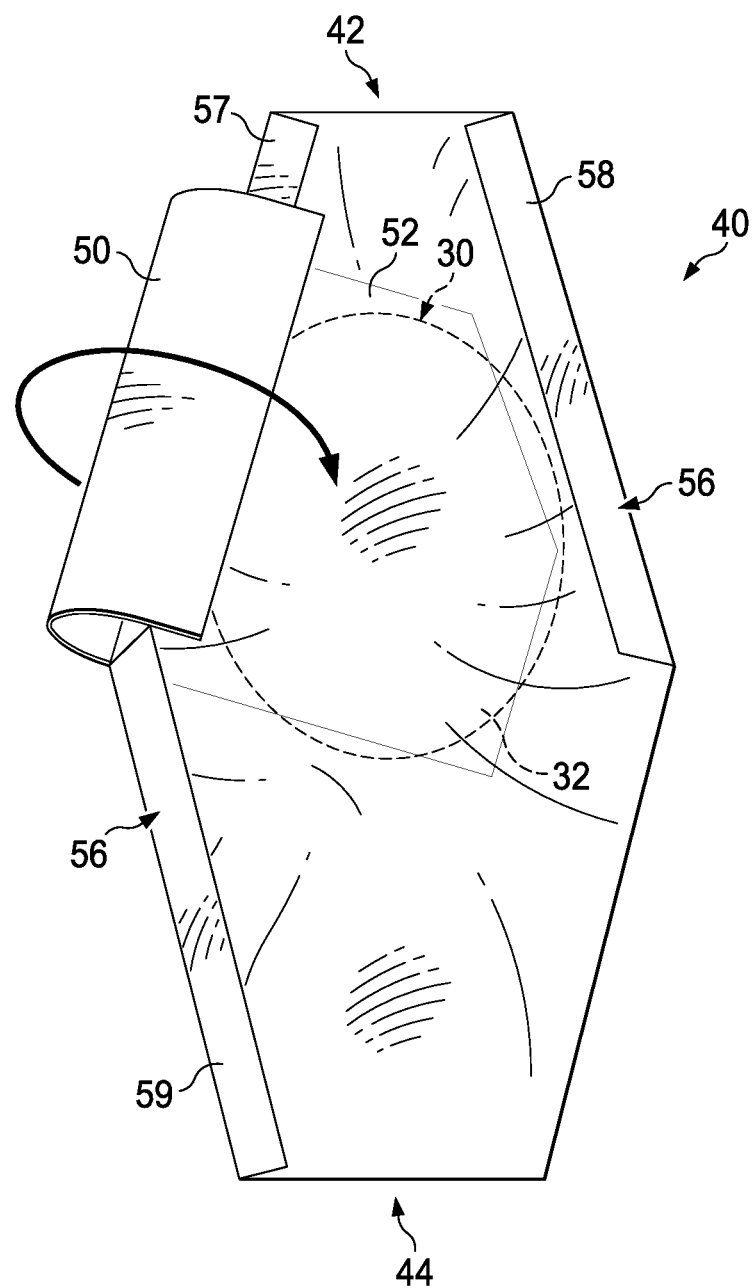

FIG. 4D: Top view of an inverse bellow, exterior tab folded over the prosthesis opening.

Figure 5:
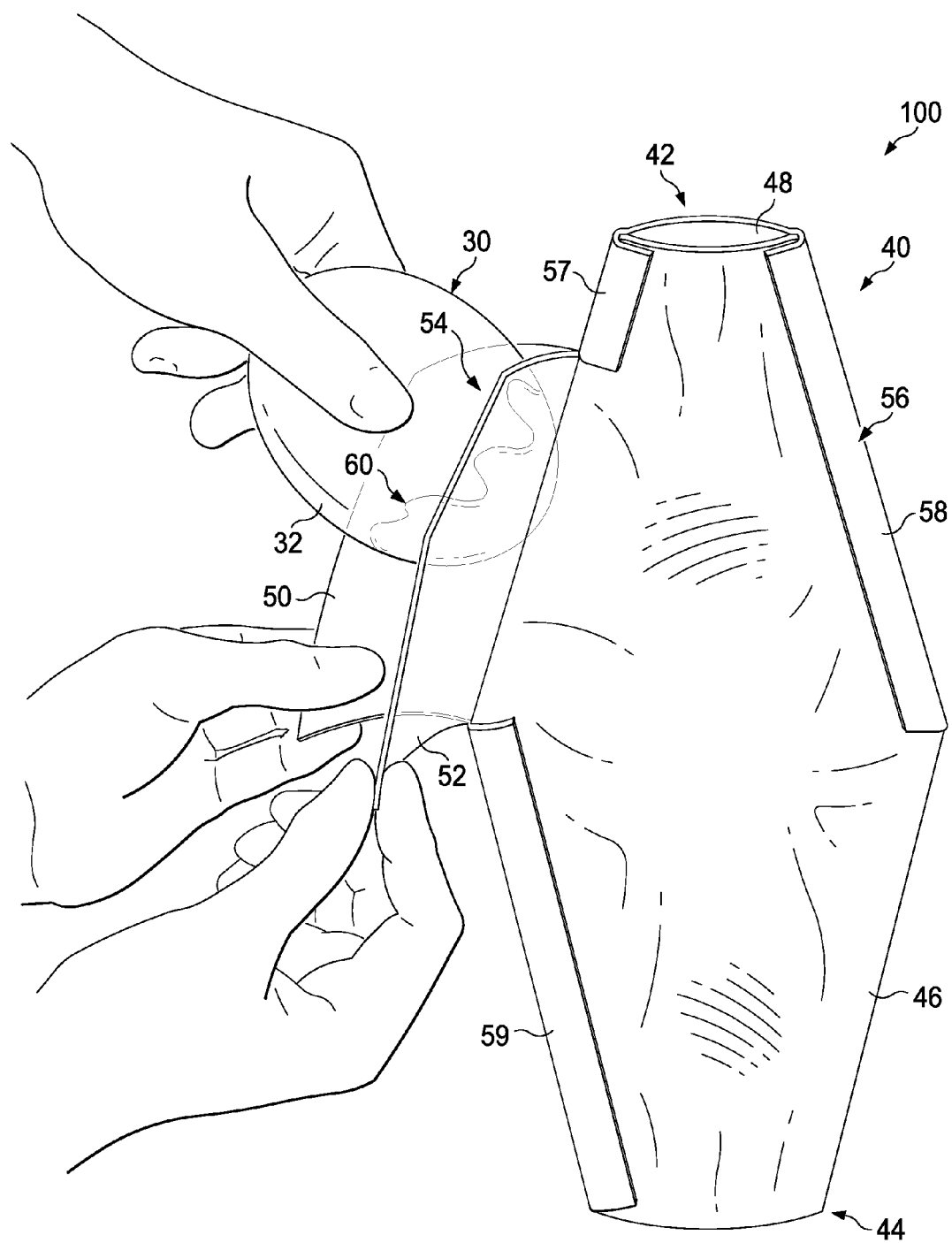

FIG. 5: Front perspective view of an inverse bellow with an implant being inserted through the prosthesis opening.

Figure 6:
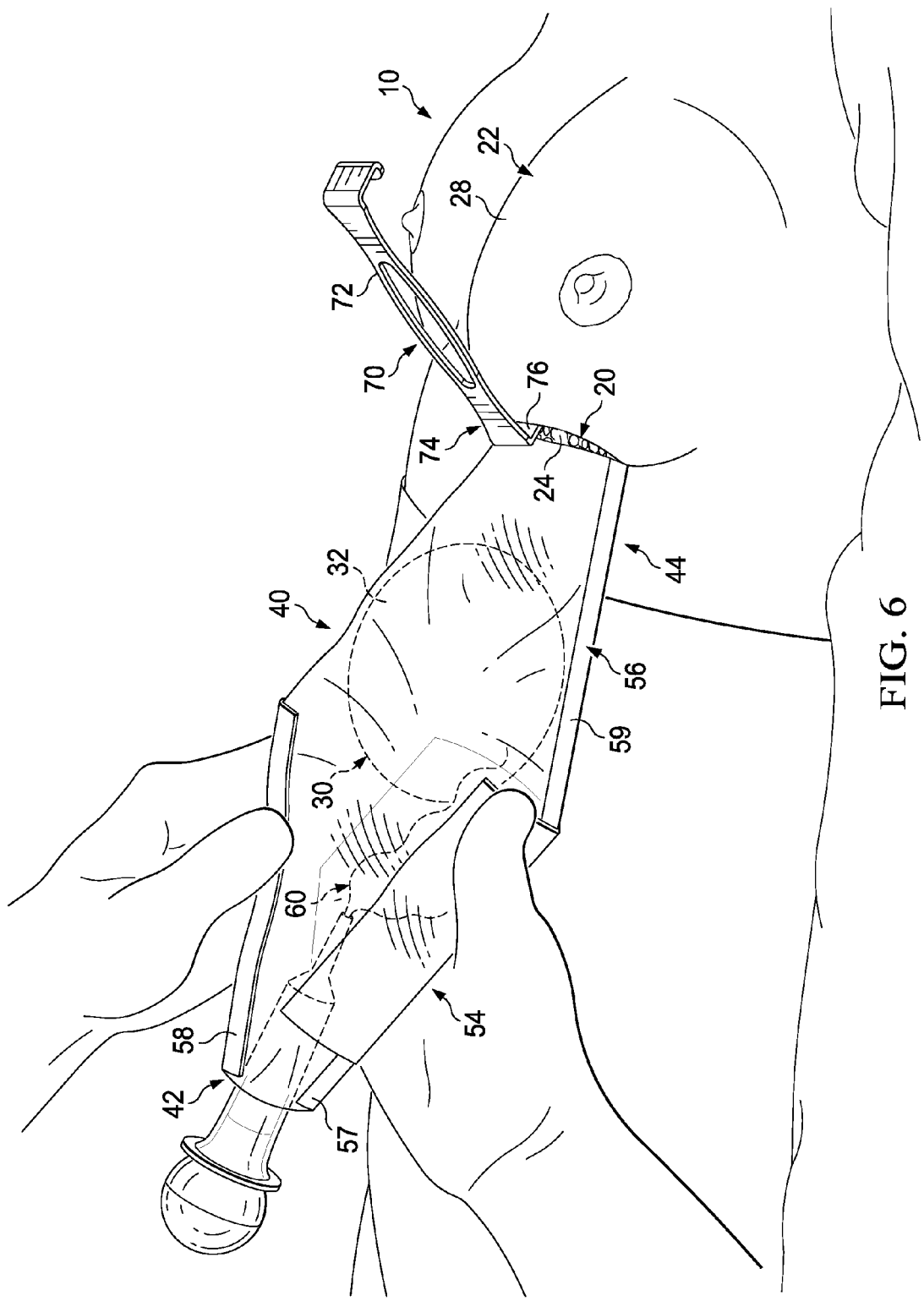

FIG. 6: Side perspective view of adding lubricant to the distal end of the inverse bellow.

Figure 7:
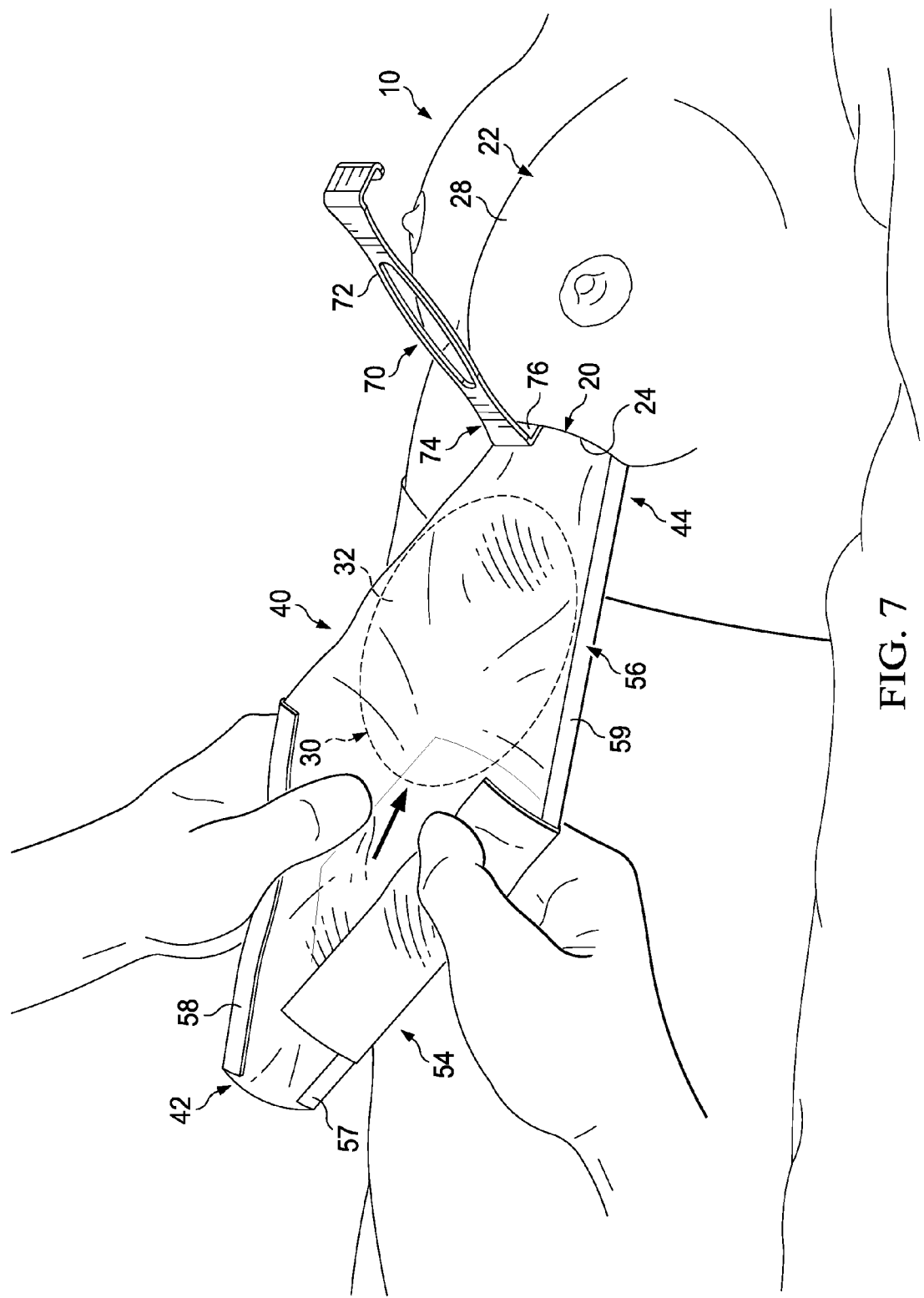

FIG. 7: Side perspective view of an inverse bellow being inserted into the patient incision.

KEY TERMS distal: the most distant portion from the point of attachment to the body
inferior: closer to the feet
lateral: a position substantially located in any side of the longitudinal position of a patient's supine position
longitudinal: a lengthwise, or the longest, direction related to the patient's supine position
proximal: the closest portion from the point of attachment to the body
superior: closer to the head of the body

REFERENCE NUMERALS IN DRAWINGS 10 patient
20 patient's incision, opening
22 patient's breast
24 patient's pocket
28 patient's skin tissue
30 prosthesis
32 breast implant
40 bellow device, bellow, inverse bellow
42 distal end, distal opening
44 proximal end, proximal opening
46 base fold
48 initial fold
50 exterior tab
52 internal tab
54 prosthesis opening
56 seal folds
57 distal short seal fold
58 distal long seal fold
59 proximal seal fold
60 lubricant
70 retractor
72 retractor handle
74 retractor handle proximal end
76 retractor proximal end lip

DETAILED DESCRIPTION OF THE DRAWINGS

Referring to the drawings, in which like numerals represent like elements,
FIGS. 1-2

FIGS. 1-2 identify individual elements of an assembled inverse bellow 40.

Referring now to FIG. 1, the top side perspective view of a bellow 40 manufactured of a sheet material such as plastic or a flexible, surgical-grade nylon. The plastic may be strengthened or reinforced with fiber. The bellow 40 may be clear, or semi-transparent in color to allow observation of the prosthesis 30 moving from bellow 40 into the patient pocket 24.

The bellow has three openings: a distal opening 42 for insertion of lubricant; a larger proximal opening 44 for insertion into the patient's incision 20; and a prosthesis opening 54, surrounded by an exterior tab 50 and an internal tab 52, for inserting the prosthesis 30 into the inverse bellow device 40. FIG. 1 shows the internal tab 52 pushed through the prosthesis opening 54, to prevent the implant from passing to the outside the bellow device 40, and the exterior tab 50 folded over the prosthesis opening 54. The exterior tab 50 can be folded and held in place by friction or attached by glue, adhesive, heat bond, surgical tape or other coupling mechanism. While FIG. 1 shows both tabs folded into working position, the bellow exterior tab 50 and bellow internal tab 52 would initially be presented to the surgeon with both tabs 50, 52 outside of the bellow 40 and surrounding the prosthesis opening 54. The tabs 50, 52 may be of the same size; or different sizes to distinguish the exterior tab 50 from the internal tab 52.

The inverse bellow 40 is assembled using the seal folds 56 which comprises distal short seal fold 57, distal long seal fold 58 and the proximal seal fold 59. In a preferred embodiment, the assembly may be done prior to packaging. In an alternate embodiment, the seal folds 56 are sealed to the base fold 46 by the patient's 10 operating team. See FIG. 4B for additional illustration of the assembly using the seal folds 56.

The bellow 40 prevents the breast implant 32 from touching the patient skin tissue 28, and also serves to prevent damage to the implant 32 during the implant 32 insertion. The most important aspect of the inverse bellow 40 is that a single unit may be manufactured to accommodate any breast implant 32 shape, volume, and diameter. This allows the manufacturer to specify the maximum outside pressure applied to the implant 32 during the insertion process. The manufacturer may also require or suggest a specific skin incision 20 length to allow insertion of the implant through the bellow 40 into the incision 20. The specifications take the burden off the surgeon to try to make shorter incisions 20. The distal end 42 of the bellow 40 can be manufactured to be smaller than the smallest implant 32 size but large enough to insert lubricant 60. This will prevent the smallest implant from inadvertently becoming dislodged though the distal end 42. The proximal end 44 of the bellow 40 is inserted through the patient opening 20 and would be manufactured to be large enough to allow passage of the largest breast implant 32 size.

FIG. 2 shows a bottom view of the manufactured version of the bellow 40 once the bellow fold 48 is folded over the base fold 46 along the abutted seam and the three seal folds 56 are completed. The manufactured bellow 40 comprises the initial fold 48 partially sealed on the periphery to the base fold 46 so that it leaves a distal opening 42, a larger proximal opening 44, a bellow prosthesis opening 54, a bellow exterior tab 50 and a bellow internal tab 52. The distal end 42 is parallel to, and smaller than, the device's proximal end.

FIGS. 3-4D

Turning to FIG. 3, the illustration depicting a perspective view of an unassembled bellow device 40. The bellow 40 form comprises two simple, convex, irregular hexagons folds 46, 48 with opposing prosthesis insertion tabs 50, 52. In a preferred embodiment, as shown in FIGS. 3-4D, the base fold 46 is manufactured abutted against the initial fold 48 along the proximal edge of the initial fold 48 from its right most angle (RMA) to the proximal right angle (PRA). In a secondary embodiment, the base fold 46 is manufactured abutted against the initial fold 48 along the distal edge of the initial fold 48 from its distal right angle (DRA) to its right most angle (RMA). In a third embodiment the initial fold 48 and base fold 46 would be separately manufactured and assembled together at a later stage. The base fold 46 and initial fold 48 attachment comprises a seal fold 56 along the abutted edges.

The initial fold 48 has an exterior tab 50 along the distal edge between the left most angle (LMA) to the distal left angle (DLA). The base fold 46 has an internal tab 52 along the distal edge between the RMA to the DRA. In an alternate embodiment, the initial fold 48 has an internal tab 52 along the distal edge between the left most angle (LMA) to the distal left angle (DLA); and the base fold 46 has an exterior tab 50 along the distal edge between the RMA to the DRA.

In the preferred embodiment, the bellow 40 would be folded along a proximal abutted edge and manufactured with three seal folds 56 along:
 a. initial fold's 48 distal edge from DLA to the first edge of the tab 50, 52;
 b. initial fold's 48 distal edge from the DRA to the RMA;
 c. initial fold's 48 proximal edge from the LMA to the proximal left angle (PLA).

In the second embodiment, the bellow 40 would be folded along a distal abutted edge and manufactured with three seal folds 56 along:
 a. initial fold's 48 distal edge from DLA to the first edge of the tab 50, 52;
 b. initial fold's 48 proximal edge from the RMA to the PRA;
 c. initial fold's 48 proximal edge from the LMA to the PLA.

In the third embodiment, the bellow 40 would be manufactured with separated initial fold 48 and base fold 46, stacked over each other and assembled with three seal folds 56 along:
 a. initial fold's 48 distal edge from the DLA to the first edge of tab 50, 52;
 b. initial fold's 48 distal edge from the DRA to the RMA;
 c. initial fold's 48 proximal edge from the LMA to the PLA;
 d. initial fold's 48 proximal edge from the RMA to the PRA.

In forth embodiment, the bellow 40 would be folded along the proximal abutted edge and manufactured with three bellow seal folds 56 along:
 a. base fold's 46 distal edge from DRA to the first edge of the tab 50, 52;
 b. base fold's 46 distal edge from the DLA to the LMA;
 c. base fold's 46 proximal edge from the RMA to the PRA.

In the fifth embodiment, the bellow 40 would be folded along the distal abutted edge and manufactured with three seal folds 56 along:
 a. base fold's 46 distal edge from DRA to the first edge of the tab 50, 52;
 b. base fold's 46 proximal edge from the RMA to the PRA;
 c. base fold's 46 proximal edge from the LMA to the PLA.

In the sixth embodiment, the bellow 40 would be manufactured with separated initial fold 48 and base fold 46, stacked over each other and assembled with three seal folds 56 along:
 a. base fold's 46 distal edge from the DRA to the first edge of the tab 50, 52;
 b. base fold's 46 distal edge from the DLA to the LMA;
 c. base fold's 46 proximal edge from the LMA to the PLA;
 d. base fold's 46 proximal edge from the RMA to the PRA.

The bellow seal folds 56 can be folded over the opposing fold 46, 48 and attached by glue, adhesive, heat bond, surgical tape or other coupling mechanism.

FIGS. 4A to 4D show the assembly of the inverse bellow 40. In FIG. 4A, the pattern is folded along the abutted edge so that base fold 48 and initial fold 46 are stacked over each other with the tabs 50, 52 pointing in the same direction.

Then in FIG. 4B, the seal folds 56 are folded over the opposing fold 46, 48 and sealed to the opposing fold 46, 48 with any desired manufacturing sealing technique.

With the breast implant 32 in place inside the inverse bellow 40, FIG. 4C, the internal tab 52 is pushed through the prosthesis opening 54. The internal tab 52 prevents the implant 32 from inadvertently ejecting through the prosthesis opening 54 during the operation.

In FIG. 4D, with the internal tab 52 inside the prosthesis opening 54, the exterior tab 50 may be pushed over the top surface of the opposing fold 46, 48. The exterior tab 50 may be sealed to the opposing fold 46, 48 with surgical tape, heat seal, instant glue, or other forms of seals. The adhered seal 50 opposes the prosthesis opening 54 and joins the initial fold 48 and base fold 46.

As illustrated in FIG. 5, in the preferred embodiment a liquid lubricant 60 surrounds the breast implant 32 inside the bellow 40. A coating of surgical lubricant 60 can be used on the inner surface of the bellow 40. As an alternative, the bellow 40 can be provided with a coating that becomes slick when wet. In still another alternative, the prosthesis 30 can be provided with a slick surface, such as a surgical lubricant 80. The surgeon also has the option of applying a lubricant 60 to the prosthesis 30 directly before inserting into the bellow 40. The lubricant 60 may also act as an antibiotic solution.

After lubrication, the breast implant 32 is inserted into the bellow device 40 by the surgeon and nurse. To do so, the nurse opens the bellow prosthesis opening 54 by separating the tabs 50, 52, and the surgeon slides the prosthesis 30 through the bellow prosthesis opening 54. The team would then fold the internal tab 52 into the bellow prosthesis opening 54 to prevent the breast implant 32 from moving back out of the opening 54. The exterior tab 50 may be left extended or folded over the opposing fold 46, 48. If desired, the exterior tab 50 may be sealed to the opposing fold 46, 48. In a preferred embodiment inserting the prosthesis 30 into the bellow device 40 would be completed prior to inserting the retractor 70 into the patient incision 20. However, a surgeon could perform this step while the bellow 40 is inserted in the incision 20.

In FIG. 6, the surgical team inserts lubricant 60 in the distal end 42 of the bellow 40. The liquid lubricant 60 surrounds the breast implant 32 inside the bellow 40 and may also simply be an antibiotic solution.

FIG. 7 shows the patient 10 placed in a supine position and an incision 20 is made in the patient's skin tissue 28. In the figure, the incision 20 is made in the inferior breast 22 crease. With the incision 20 opened, the surgeon can then form a pocket 24 in one of two places under the breast 22: subglandular (between the breast 22 tissue and pectoralis muscle) or subpectoral (under the pectoralis muscle). The pocket 24 is then sized to receive the prosthesis 30. A retractor 70 is then inserted with the retractor handle proximal end 74 and the retractor proximal lip 76 used to retract the incision 20 and hold the incision 20 open. The surgeon opens the incision 20 by manipulating the retractor handle 72.

The retractor 70 assembly comprises a handle 72 located in the center, retractor handle proximal end 74, and retractor handle proximal end lip 76. The retractor 70 can have various shapes and sizes to match the particular application or surgeon preferences. The handle 72 of the retractor 70 is bent or angled on the ends relative to the intermediate portion. The proximal end 74 in the retractor 70 has a lip 76 that is angled relative to the end 74. The retractor 70 is made of metal, such as stainless steel but can also be manufactured in a surgical plastic.

The retractor proximal end 74 is structured and arranged to be inserted through the incision 20 into a pocket 24 of a patient 10. The proximal end lip 76 helps maintain the proximal end 74 of the retractor 70 beneath skin tissue 28 of a patient 10.

The retractor 70 extends laterally from the inverse bellow 40, so as not to interfere with the surgeon manipulating the bellow 40, with the proximal ends of the retractor 74 and proximal end lip 76 inserted into the incision 20 and located under the skin tissue 28 and moved to retract the incision 20. The inverse bellow 40 may be lubricated with a lubricant 60 and inserted into the open incision 20.

The bellow 40, distal to the prosthesis 30, is squeezed and/or twisted to force the prosthesis 30 toward the proximal end 44 of the bellow device 40 and into the pocket 24. The prosthesis 30 deforms to fit through the proximal opening 44.

Once the prosthesis 30 is located inside the pocket 24, the retractor 70 is removed from the incision 20, followed by the bellow 40. The incision 20 can then be closed.

If bellow 40 is designed for reuse, they are subjected to sterilization procedures. If the bellow 40 is designed for single use, they are disposed of. An advantage of the inverse bellow 40 and method is that the implant 32 and distal opening 42 can be properly sized during manufacture with respect to each other so that the smallest breast implant 32 cannot be inadvertently expelled from the distal end 42 of the device 40. For example, some implants 32 are physically large and require an insertion device with a larger diameter proximal opening 44, while other implants 32 are physically smaller and can also exit proximal opening 44. By sizing the distal end 42 smaller than the size of the smallest implant 32, and the proximal end 44 large enough to allow passage of the largest implant 32, any size implant 32 can only exit through the proximal opening 44 and into the patient's pocket 24.

The implant 32 is subject to damage if the implant 32 is mishandled. Possible mishandling includes subjecting the implant 32 to undue stresses or pressures, such as may be caused by attempting to squeeze the implant 32 through an opening 20 that is too small, and folding of the external silastic shell, internal fracture of the cohesive silicone gel. A surgeon may make an incision 20 in the patient 10 that is too small for the implant 32 and thus too much force is required to squeeze the implant 32 into the pocket 24. With the apparatus, the implant 32 is protected from damage by the provision an adequate skin incision length and of the properly sized proximal end 44. The major complication with implants 32 is capsular contracture thought to be due to sub-clinical infection. Sub-clinical infection is most likely caused by pushing the implant 32 through the skin incision 20, dragging natural skin 28 bacteria (still present after proper skin 28 preparations) into the pocket 24 surgically created for the implant 32. Use of this device 40 prevents the implant 32 from coming in contact with the skin tissue 28 during the insertion process.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

In the foregoing description, and the following claims, method steps and/or actions are described in a particular order for the purposes of illustration. It should be appreciated that in alternate embodiments, the method steps and/or actions may be performed in a different order than that described. Additionally, the methods described above may be embodied in machine-executable instructions stored on one or more machine-readable mediums, such as disk drives, thumb drives or CD-ROMs. The instructions may be used to cause the machine (e.g., computer processor) programmed with the instructions to perform the method. Alternatively, the methods may be performed by a combination of hardware and software. While illustrative and presently preferred embodiments of the invention have been described in detail herein, it is to be understood that the inventive concepts may be otherwise variously embodied and employed, and that the appended claims are intended to be construed to include such variations, except as limited by the prior art.

Benefits, other advantages, and solutions to problems have been described herein with regard to specific embodiments. However, the advantages, associated benefits, specific solutions to problems, and any element(s) that may cause any benefit, advantage, or solution to occur or become more pronounced are not to be construed as critical, required, or essential features or elements of any or all the claims of the invention. As used herein, the terms "comprises", "comprising", or any other variation thereof, are intended to cover a non-exclusive inclusion, such that a process, method, article, or apparatus composed of a list of elements that may include other elements not expressly listed or inherent to such process, method, article, or apparatus.

ADVANTAGES

From the description above, a number of advantages become evident for the "Inverse Bellow Insertion Device." The present invention provides all new benefits for participating parties including manufacturers, patients and surgeons:
   a) allow manufacturers to ship a single size bellow for all implant sizes;
   b) allows patient's a lower risk of complications;

c) allows doctors to prevent contamination by skin bacteria, gross infection, resulting in infection and/or capsular contracture;
d) allows doctors to eliminate the step of trimming the insertion device;
e) allows doctors to eliminate damage to the implant during the insertion process;
f) allows doctors a simplified insertion process.

The invention claimed is:

1. An apparatus for inserting a prosthesis through an incision into a surgical pocket, comprising: a bellow formed of two convex, irregular hexagon folds with opposing tabs; an initial fold abutted to a base fold along the proximal right edge from the initial fold's right most edge to proximal right edge; the initial fold folded over the base fold along the abutted edge; a distal short seal fold along the initial fold's distal left angle to the edge of a tab; a distal long seal fold along the initial fold's distal edge from the distal right angle to the right most angle; a proximal seal fold along the initial fold's proximal edge from the left most angle to the proximal left angle;

whereby an inverse bellow is formed with a bellow prosthesis opening, a proximal opening and a smaller distal opening.

2. An apparatus for inserting a prosthesis through an incision into a surgical pocket, comprising: a bellow formed of two convex, irregular hexagon folds with opposing tabs; an initial fold abutted to a first fold along the distal right edge from the initial fold's distal right edge to right most edge; the base fold folded over the initial fold along the abutted edge; a seal fold along the base fold's distal right angle to the edge of a tab; a seal fold along the base fold's proximal edge from the left most angle to the proximal left angle; a seal along the base fold's proximal edge from the right most angle to the proximal right angle;

whereby an inverse bellow is formed with a bellow prosthesis opening, a proximal opening and a smaller distal opening.

3. An apparatus for inserting a prosthesis through an incision into a surgical pocket, comprising: an base fold of a convex, irregular hexagon with a tab; an initial fold of a convex, irregular hexagon with a tab; the first fold stacked over the initial fold; a seal along the initial fold's distal left angle to the edge of a tab; a seal along the initial fold's distal edge from the distal right angle to the right most angle; a seal along the initial fold's proximal edge from the left most angle to the proximal left angle; a seal along the initial fold's proximal edge from the right most angle to the proximal right angle;

whereby an inverse bellow is formed with a bellow prosthesis opening, a proximal opening and a smaller distal opening.

* * * * *